United States Patent
Kraus et al.

(10) Patent No.: US 8,054,446 B2
(45) Date of Patent: Nov. 8, 2011

(54) EUV LITHOGRAPHY APPARATUS AND METHOD FOR DETERMINING THE CONTAMINATION STATUS OF AN EUV-REFLECTIVE OPTICAL SURFACE

(75) Inventors: Dieter Kraus, Oberkochen (DE); Dirk Heinrich Ehm, Lauchheim (DE); Stefan-Wolfgang Schmidt, Aalen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 516 days.

(21) Appl. No.: 12/196,075

(22) Filed: Aug. 21, 2008

(65) Prior Publication Data

US 2010/0045948 A1 Feb. 25, 2010

(51) Int. Cl.
*G03B 27/52* (2006.01)
*G03B 27/42* (2006.01)
(52) U.S. Cl. .......................... 355/30; 355/53
(58) Field of Classification Search .......... 355/30, 355/53, 67; 356/237.3; 250/492.2
See application file for complete search history.

(56) References Cited

U.S. PATENT DOCUMENTS

| | | | |
|---|---|---|---|
| 6,642,994 B2 * | 11/2003 | Mori et al. | 355/53 |
| 6,846,086 B2 * | 1/2005 | Goldstein | 359/846 |
| 6,847,463 B2 | 1/2005 | Malinowski | |
| 7,012,696 B2 * | 3/2006 | Orr et al. | 356/454 |
| 7,084,982 B2 | 8/2006 | Yamamoto et al. | |
| 7,087,907 B1 * | 8/2006 | Lalovic et al. | 250/461.1 |
| 7,145,641 B2 * | 12/2006 | Kroon et al. | 355/71 |
| 2004/0227102 A1 * | 11/2004 | Kurt et al. | 250/491.1 |

FOREIGN PATENT DOCUMENTS

WO 2008/034582 A2 3/2008

OTHER PUBLICATIONS

"Optical Lossmeters" Los Gatos Research, www.lgrinc.com.

* cited by examiner

*Primary Examiner* — Hung Henry Nguyen
(74) *Attorney, Agent, or Firm* — Sughrue Mion, PLLC

(57) ABSTRACT

The invention relates to an EUV lithography apparatus with at least one EUV-reflective optical surface and a cavity ring-down reflectometer adapted to determine the contamination status of the EUV-reflective optical surface for at least one contaminating substance by determining the reflectivity of the EUV-reflective optical surface for radiation at a measuring wavelength ($\lambda_m$). The invention further relates to a method for determining the contamination status of at least one EUV-reflective optical surface arranged in an EUV lithography apparatus for at least one contaminating substance comprising determining the reflectivity of the EUV-reflective optical surface for radiation at a measuring wavelength ($\lambda_m$) using a cavity ringdown reflectometer.

15 Claims, 4 Drawing Sheets

EUV LITHOGRAPHY APPARATUS AND METHOD FOR DETERMINING THE CONTAMINATION STATUS OF AN EUV-REFLECTIVE OPTICAL SURFACE

BACKGROUND OF THE INVENTION

The invention relates to an EUV lithography apparatus, and to a method for determining the contamination status of at least one EUV-reflective optical surface for at least one contaminating substance, the EUV-reflective optical surface being arranged in an EUV lithography apparatus.

Optical elements used in EUV lithography apparatuses are typically reflective elements, as no optical materials are known which can provide sufficient transmission for radiation at EUV wavelengths, typically in a range from about 5 nm to about 20 nm. In such EUV lithography apparatuses, it is necessary to operate the EUV-reflective optical elements in a vacuum because the service life of the EUV-reflective elements is limited by contaminating substances which may deposit on their EUV-reflective surfaces. In the context of the present application, contaminating substances are defined as substances which are susceptible to form deposits on the optical surfaces, and in particular when exposed to EUV-radiation. In this respect, hydrocarbons having an atomic mass of about 40 amu or above are considered as contaminating substances, whereas hydrocarbons having an atomic mass below 40 amu, e.g., methane ($CH_4$), usually stay volatile even when irradiated with EUV light and do not form such deposits.

The contamination of EUV-reflective optical surfaces has an adverse effect on the performance of the EUV lithography apparatus as a whole, as such, contamination affects the optical properties of the optical components and may cause a loss in reflectivity or introduce wavefront errors. Therefore, control and knowledge of the contamination status of EUV-reflective optical elements is desired. In this respect, US 2004/0227102 A1, U.S. Pat. Nos. 6,847,463 B2, and 7,084,982 B2 disclose a measuring unit for determining the contamination status of an EUV-reflective optical surface, the measuring unit comprising a light source (e.g. a LED) for emitting light to the EUV-reflective optical surface, and an optical sensor for detecting the intensity of the light reflected from the EUV-reflective optical surface. In such a way, the contamination status, and in particular, the thickness of a contamination layer on EUV-reflective optical surfaces, may be determined.

For determining the reflectivity or transmission of optical elements for the visible wavelength range, it is known to use a technique which is referred to as cavity ringdown spectrometry. A cavity ringdown spectrometer typically comprises a laser source, an optical resonator, and a detection unit for detecting the laser radiation reflected or transmitted by the optical element, as described, e.g., on the website of the company "Los Gatos Research" www.lgrinc.com. Cavity ringdown spectroscopy involves measuring the decay of laser light in the optical resonator after the laser is rapidly switched off. The decay curve is an exponential curve with a time constant $\tau$ from which the reflectivity or transmission of the optical element may be deduced. In such a way, the reflectivity and/or transmission of optical elements for the visible wavelength range can be determined with high precision.

As indicated in WO 2008/034582 A2, it is known to use cavity ringdown spectroscopy for the determination of partial pressures of contaminating gaseous species in an EUV lithography apparatus. In such case, the absorption of the gaseous species for the radiation inside the optical resonator is determined, thus allowing an artisan to deduce the concentration of the absorbing gaseous species in the resonator, and to gain information about the partial pressure of that gaseous species in the EUV lithography apparatus, and in particular, close to the EUV-reflective optical surfaces. However, for measuring the contamination status of the EUV-reflective optical surfaces themselves, WO 2008/034582 A2 suggests the approach described, e.g., in US 2004/0227102 A1, U.S. Pat. Nos. 6,847,463 B2, and 7,084,982 B2, cited above.

SUMMARY OF THE INVENTION

The present invention provides an EUV lithography apparatus and a method for determining the contamination status of an EUV-reflective optical element with high precision.

According to one aspect of the invention, the EUV lithography apparatus comprises at least one EUV-reflective optical surface, and a cavity ringdown reflectometer adapted to determine the contamination status of the EUV-reflective optical surface for at least one contaminating substance by determining the reflectivity of the EUV-reflective optical surface for radiation at a measuring wavelength.

The inventors have found that the cavity ringdown technique, which is typically used for determining the optical properties, and in particular the reflectivity, of optical elements for the visible wavelength range may be advantageously used for determining the contamination status of EUV-reflective optical elements due to its high sensitivity. In particular, the cavity ringdown technique may be adapted for selectively determining the contamination status of EUV-reflective optical surfaces for specific contaminating substances, as will be described below. By measuring the intensity of the radiation reflected from the EUV-reflective optical element at the measuring wavelength, the decay time constant $\tau$, and thus the reflectivity of the optical surface, can be determined. It will be understood that it is also possible to perform a sequence of measurements in order to determine a change of the time constant $\tau$, and thus a change of the reflectivity over time.

The cavity ringdown technique allows determining the contamination status of EUV reflective optical surfaces with increased precision as compared to the reflectivity measurement technique described, e.g., in US 2004/0227102 A1, as the optical resonator (cavity) drastically increases the sensitivity of the measurement, due to the radiation being reflected and detected a large number of times in the optical resonator during the performance of the measurement.

Preferably, the measuring wavelength is adjustable depending on the contaminating substance. In such case, a laser with variable wavelength may be used, the wavelength of the laser being adjustable to a wavelength at which the contaminating substance has an absorption maximum. In such a way, it is possible to increase the sensitivity of the measurement for specific contaminating substances.

Typically, the measuring wavelength is larger than 200 nm, in particular larger than 250 nm. The contamination status of the EUV-reflective optical element may be determined from the reflectivity at a measuring wavelength which is different from the wavelength of the EUV radiation. Typically, an EUV-reflective optical surface is also reflective for higher wavelengths, in particular for wavelengths in the visible wavelength range.

In a preferred embodiment, the cavity ringdown reflectometer comprises an optical resonator, and the EUV-reflective optical surface is arranged in the optical path of the optical resonator. Typically, apart from the EUV-reflective optical surface, the optical resonator comprises two end mirrors as optical elements which are reflective for radiation at the measuring wavelength and which delimit the optical resonator. Both of the end mirrors are typically semi-transparent, one of the end mirrors serving to inject the laser radiation into the optical resonator, the other mirror serving to extract the radiation from the optical resonator for providing it to a detector element.

In a preferred embodiment, the cavity ringdown reflectometer comprises a movement mechanism for moving the EUV-reflective optical surface into the optical path of the optical resonator. In this case, during the exposure process, the EUV-reflective optical surface is typically arranged in a rest position located out of the optical paths of both the EUV light source and the optical resonator. During pauses in the exposure process, the EUV-reflective optical surface may then be moved into a measurement position, in which the EUV-reflective optical surface is typically arranged in an overlap region of the optical paths of the EUV light source and the optical resonator. In such a way, when switching-on the EUV light source, the contamination status of the EUV-reflective optical surface may be determined under exposure to EUV radiation without the EUV-reflective optical surface taking part in the exposure process. Thus, the temperature of the EUV-reflective optical surface may be changed (see below) for adsorbing/desorbing contaminating substances without the risk of degrading the optical performance of the lithography apparatus. In such a way, and in particular when a vacuum in the EUV lithography apparatus has to be (re-)established before the start-up of the exposure process, the EUV-reflective surface may serve as a test surface for checking if the number of contaminants in the EUV lithography apparatus is small enough to start the exposure. If this is the case, the EUV-reflective optical surface can be moved back to its rest position and the exposure process may be initiated. Moreover, in its measurement position, the EUV-reflective optical surface may be arranged in such a way that it blocks the optical path from the EUV light source to the optical elements following the EUV-reflective surface in the EUV lithography apparatus, thus protecting them from possible degradations caused by the exposure to EUV radiation when a large number of contaminants are present during the re-establishment of the vacuum.

Preferably, the optical resonator is a ring resonator. In a ring resonator, the optical path of the radiation at the measuring wavelength forms a loop, such that three or more mirrors are required to form a ring resonator. In such a resonator, the angles of incidence of the radiation incident to the individual mirrors may be chosen to be larger as compared to linear resonators having the same number of mirrors, which may improve the sensitivity of the reflectivity measurement, depending on the type of coating material used for the mirrors. Moreover, the number of reflections inside the ring resonator may be increased as compared to a linear resonator, thus also enhancing the sensitivity of the measurement.

In another preferred embodiment, the cavity ringdown reflectometer comprises a laser source for generating the radiation at the measuring wavelength and a detection unit for measuring the intensity of the radiation reflected from the EUV-reflective surface. Typically, a laser source is used for performing the cavity ringdown technique, and the detection unit is a photodetector which is adapted to detect radiation at the measuring wavelength.

In a preferred embodiment, the EUV lithography apparatus further comprises a temperature adjusting unit for adjusting the temperature of at least one optical surface of an optical element of the optical resonator, and in particular, of the EUV-reflective optical surface. The temperature adjusting unit may comprise one or more heating and/or cooling elements which are in thermal contact with the EUV-reflective optical surface for performing temperature adjustment. The heating/cooling elements may be heated filaments, channels with cooling/heating liquids, Peltier elements, etc. It will be understood that when an EUV reflective optical surface arranged in the optical path of the light source is exposed to EUV radiation, a temperature change of the EUV-reflective optical element may affect its optical properties, which may have an adverse effect on the exposure process, depending on the position of the optical element in the EUV lithography apparatus. In such case, it is advantageous to perform the temperature adjustment on an optical surface of the optical resonator which does not take part in the exposure process, e.g. an optical surface of the end mirrors, which is not necessarily reflective for EUV radiation, and which is typically not arranged in the optical path of the EUV light source. It will be understood that in this case, the temperature adjustment does not allow determination of the contamination status for substances which are only generated under exposure to EUV radiation.

Preferably, the temperature adjusting unit is adapted to adjust the temperature of at least one optical surface of an optical element of the optical resonator, in particular of the EUV-reflective optical surface, depending on the contaminating substance. In such case, the temperature of the optical surface may be controlled by the temperature adjusting unit for increasing or decreasing the adsorption of specific contaminating substances contained in the residual gas atmosphere of the EUV lithography apparatus. When raising the temperature of the EUV-reflective optical element above the condensation temperature of a specific contaminating substance, the latter desorbs from the optical surface and an abrupt change in the decay curve may be observed. Thus, when continuously monitoring the decay curves during such a temperature change, the resulting change in reflectance can provide information about the contamination status of the optical element with respect to that specific contaminant, e.g. by comparing the change in reflectance with calibration data which has previously been measured under controlled conditions. In the same way, by cooling down the optical element below the condensation temperature of a specific contaminant, the resulting loss in reflectivity may be observed for determining the contamination status of the EUV-reflective optical surface for that contaminant.

Preferably, the EUV-reflective optical surface is exposed to EUV radiation. Typically, the EUV-reflective optical surface is arranged in the optical path of an EUV light source and the contamination status of the EUV-reflective optical element can be determined in-situ, and possibly also in operando, i.e. during the exposure process.

In a preferred embodiment, the EUV-reflective optical surface is arranged in an irradiated area outside of an optical path of an EUV light source. In such case, the EUV-reflective optical surface may serve as a sample element and may be disposed in an overexposed region in the EUV lithography apparatus, i.e. a region that is irradiated with EUV light but is arranged outside of the optical path of the EUV light source. In such a way, the temperature of the EUV-reflective optical surface may be changed for adsorbing/desorbing contaminating substances without the risk of degrading the optical performance of the lithography apparatus. In particular, the overexposed region with the EUV-reflective optical surface may be arranged adjacent to a further EUV-reflective optical surface which is arranged within the optical path; both EUV-reflective optical surfaces are preferably arranged on the same optical element. In such a way, both EUV-reflective surfaces are operated under similar conditions with respect to the incident EUV radiation, such that determining the contamination status of the sample surface arranged outside of the optical path is also indicative of the contamination status of the further EUV-reflective optical surface which is arranged inside the optical path.

In a preferred embodiment, the lithography apparatus further comprises a cleaning arrangement for cleaning at least one EUV-reflective optical surface, the cleaning arrangement being controlled depending on the contamination status of the EUV-reflective optical surface. In particular, the progress of the cleaning may be observed by an increase of the reflectivity of the EUV-reflective optical element. When a cleaning process is used which does not only remove the contaminating substances but may also affect the EUV-reflective optical surface, e.g. when cleaning with a reactive gas such as activated/atomic hydrogen, the cleaning should be terminated as soon as the contaminating substances are entirely removed from the optical surface. The precise endpoint of the cleaning may be determined when the contamination status of the optical element is provided as a feedback signal to the cleaning arrangement.

A further aspect of the invention relates to a method for determining the contamination status of at least one EUV-reflective optical surface for at least one contaminating substance, the EUV-reflective optical surface being arranged in an EUV lithography apparatus, the method comprising determining the reflectivity of the EUV-reflective optical surface for radiation at a measuring wavelength using a cavity ringdown reflectometer. The method allows for characterization of the optical element with respect to its contamination status inside of the EUV lithography apparatus, and may in particular be used to determine the contamination status of the optical surface during the exposure process.

In preferred variants of the method, the measuring wavelength and/or the temperature of at least one optical surface of an optical element of the optical resonator is/are adjusted, preferably depending on the contaminating substance. In this way, the contamination status may be determined with respect to different contaminating substances. In particular, for determining the contamination status with respect to a given number of contaminating substances, the temperature and/or the measuring wavelength may be continuously changed in an oscillating manner between a an upper and a lower limit, these limits being selected such that the condensation temperatures and/or absorption maxima of the contaminating substances in question are arranged in the range between these limits. Moreover, for determining the reflectivity of the EUV-reflective optical surface, the EUV-reflective optical surface may be moved into the optical path of an optical resonator of the cavity ringdown reflectometer.

Further features and advantages are stated in the following description of exemplary embodiments, with reference to the figures of the drawing which shows significant details, and are defined by the claims. Individual features can each be used singly, or several of them can be taken together in any desired combination, in order to implement desired variations.

DETAILED DESCRIPTION OF THE INVENTION

Figure 1A:
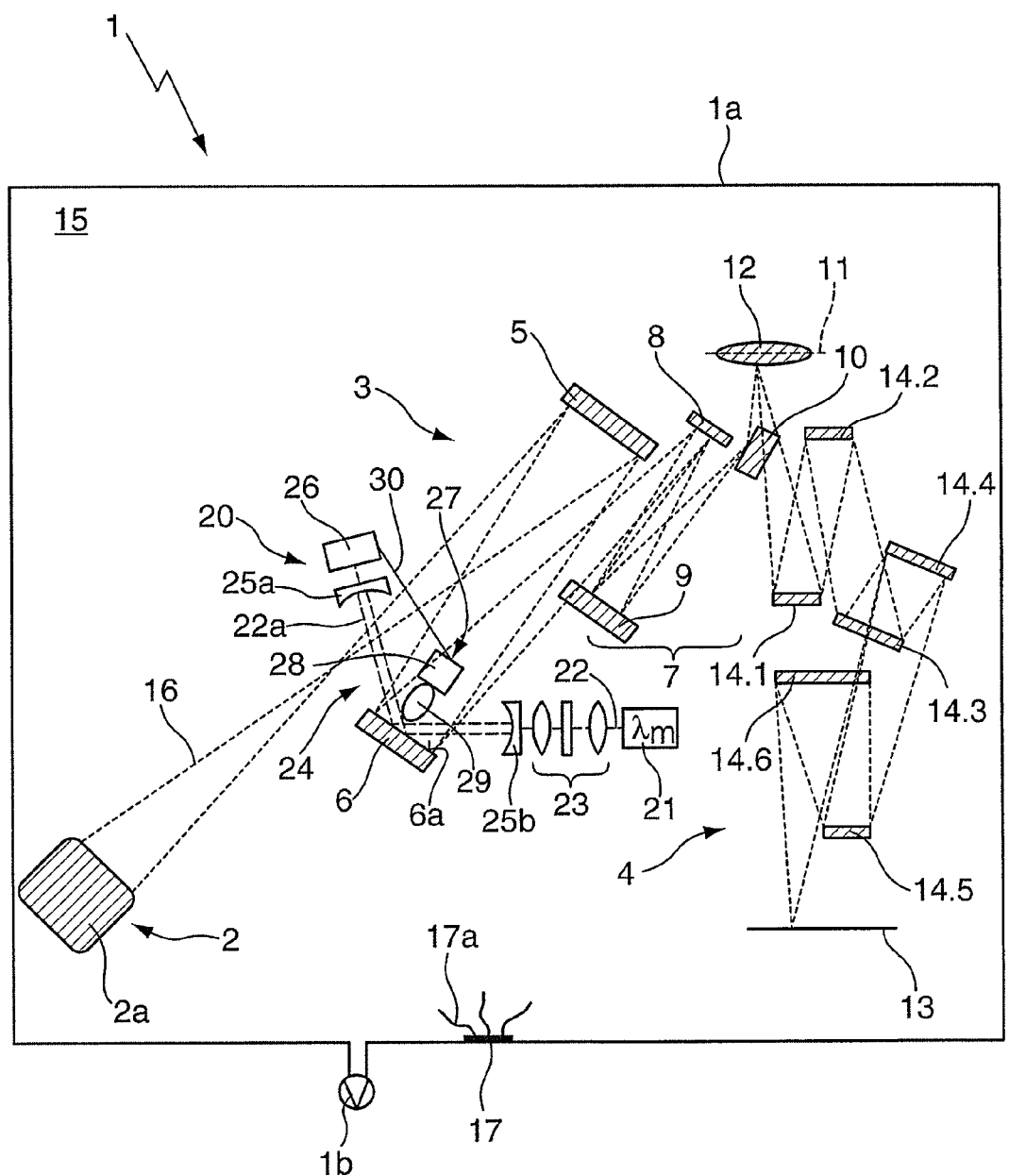
FIGS. 1a-c are diagrammatic views of three embodiments of the inventive EUV lithography apparatus comprising a cavity ringdown reflectometer.

FIG. 1a shows a diagrammatic view of an EUV lithography apparatus 1, comprising a housing 1a which is associated with a vacuum generating unit 1b (vacuum pump). The EUV lithography apparatus 1 comprises a beam shaping system 2, an illumination system 3 and a projection system 4 which are arranged one after the other in a beam path 16 which emanates from an EUV light source 2a of the beam shaping system 2. The EUV light source 2a may be implemented, e.g., as a plasma source or a synchrotron. The radiation emanating from the light source 2a in a wavelength range of between approximately 5 nm and approximately 20 nm is first shaped in a collimator (not shown), and then filtered in a monochromator to produce the desired operating wavelength, typically about 13.5 nm, the radiation at this wavelength forming the beam path 16.

The illumination system 3 comprises a mirror 5 with field raster elements and a mirror 6 with pupil raster elements. A group of three mirrors, arranged downstream and acting as a telescopic lens 7 comprises a first and a second mirror 8, 9 which are operated under normal incidence, as well as a third mirror 10, onto which mirror the light impinges at glancing incidence. The illumination system 3 generates as homogeneous an image field as possible in an object plane 11 in which a reticle 12 with a structure (not shown) that is to be imaged at reduced size is arranged.

The projection system 4 is used to image the structure arranged on the reticle 12 in the object plane 11 onto an image plane 13, in which image plane 13 a wafer with a photosensitive layer (not shown) is arranged. For reduced-size imaging, the projection system 4 comprises six further mirrors 14.1 to 14.6 as reflective optical elements.

In the housing 1a, the vacuum generating unit 1b generates a vacuum having an overall pressure of approximately $10^{-5}$ mbar or above, and a partial pressure of hydrocarbons (at or above 40 amu) of about $10^{-12}$ mbar or below. However, this vacuum is insufficient to effectively prevent the deposit of contaminating substances such as the above-mentioned hydrocarbons on the EUV-reflective surfaces of the mirrors 5, 6, 8 to 10, 14.1 to 14.6 and on the reticle 12. The contaminating substances 17a may in particular be outgassed from components 17 which are arranged inside of the housing 1a which are made of materials which are not bakeable.

The contaminating substances 17a, especially hydrocarbons at 40 amu or above, may react with the material of the EUV-reflective surfaces of the mirrors 5, 6, 8 to 10,14.1 to 14.6, and, in particular when these surfaces are irradiated with EUV radiation, non-volatile deposits may be formed on the EUV-reflective surfaces, which may lead to a deterioration of their optical properties, in particular to a loss of reflectivity. Consequently, the contamination status of the EUV-reflective optical surfaces of the mirrors 5, 6, 8 to 10, 14.1 to 14.6 may be determined by measuring their reflectivity.

For this purpose, a cavity ringdown reflectometer 20 is arranged in the housing 2, in the example shown in FIG. 1a being adapted to measure the reflectivity of the second mirror 6 of the illumination system 3. The cavity ringdown reflectometer 20 comprises a laser light source 21 for emitting laser radiation 22 at a measuring wavelength $\lambda_m$ in the UV, visible or IR wavelength range. For example, laser diodes may be used as a light source 21 operating, e.g., at a measuring wavelength $\lambda_m$ of 405 nm (blue), 523 nm (green) or 633 nm (red). The laser light source 21 typically is a pulsed laser source. In particular, a variable-frequeancy laser source may be adapted to change the measuring wavelength $\lambda_m$ continuously over a pre-defined wavelength range.

The laser radiation 22 emitted from the laser source 21 is fed to the input optics 23 for coupling the laser radiation 22 into an optical resonator 24. The optical resonator 24 is a linear resonator which comprises two end mirrors 25a, 25b limiting the optical path 22a of the laser radiation 22 in the optical resonator 24. A detection unit 26 in the form of a photodetector and associated circuitry (data-acquisition/analysing system) is provided at the end of the optical resonator 24 adjacent to the first mirror 25a. The EUV-reflective optical surface 6a of the second mirror in the illumination system 3 forms part of the optical path 22a in the optical resonator 24 and reflects the laser radiation 22 at the measuring wavelength $\lambda_m$.

For determining the contamination status of the EUV-reflective optical surface 6a of the mirror 6, first the laser light source 21 is set to a measuring wave-length $\lambda_m$ that corresponds to a maximum in the absorption spectrum of the contaminating substance for which the contamination status is to be determined. Subsequently, a laser pulse is generated which enters the optical resonator 24 by way of the input optics 23. The intensity I of the laser pulse over time (represented in FIGS. 3a and 3b) extracted from the optical resonator 24 by the first mirror 25a is monitored in the detection unit 26. The intensity of the laser pulse is an exponential given by the following equation:

$$I(t) = I_0 \exp(t/\tau),$$

wherein the time constant $\tau$ of the exponential decay provides information about the absorption of the laser pulse in the optical resonator 24, the absorption being dependent on the reflectivity of the EUV-reflective optical surface 6a.

Figure 3A:
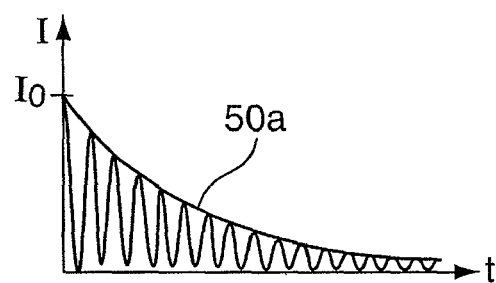
FIGS. 3a and 3b are two intensity curves of the decay behaviour of laser pulses of the cavity ringdown reflectometer of FIGS. 1a,b.
Figure 3B:
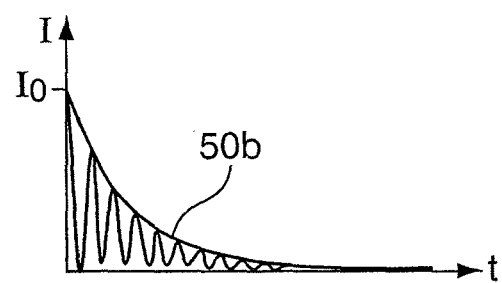

FIG. 3a shows a first decay curve 50a of the intensity I of the radiation inside the optical resonator 24 without the presence of contaminating substances on the EUV-reflective optical surface 6a. Thus, the first decay curve 50a may used for calibrating the reflectometer 20. FIG. 3b shows a second decay curve 50b which has been detected after a considerable amount of contaminating substances has been deposited on the EUV-reflective optical surface 6a.

The comparison of the diagrams of FIGS. 3a and 3b clearly shows that when one or a plurality of contaminating substances is deposited on the EUV-reflective optical surface 6a, the life-time of the photons in the optical resonator 24 is reduced. Consequently, the value of the time constant $\tau$ of the exponential decay is an indicator for the reflectivity and thus for the contamination status of the EUV-reflective optical surface 6a. As compared to an ordinary reflectivity measurement, the cavity ringdown method is much more sensitive to the amount of contaminations on the optical element, as the laser radiation 22, which is used for the reflectivity measurement, is reflected typically several thousand times in the optical resonator 20. Moreover, as all of the components of the cavity ringdown reflectometer 20 may be arranged outside of the optical path 16 of the EUV radiation, the contamination status of the EUV-reflective optical surface 6a may be determined in operando, i.e. during the exposure process.

Moreover, as is also shown in FIG. 1a, the information about the contamination status of the EUV-reflective optical surface 6a may be used as an input to a cleaning arrangement 27 which may be implemented in the way described in detail in PCT/EP2007/009593, the entire contents of which are incorporated herein by reference. The cleaning arrangement 27 comprises a cleaning head 28 which directs a jet 29 of cleaning gas, and in particular, atomic hydrogen, to the EUV-reflective optical surface 6a. The jet 29 of cleaning gas removes the contaminating substances, typically deposited in the form of a contamination layer, from the EUV-reflective optical surface 6a. In order to monitor the progress of the cleaning, decay curves of the type shown in FIGS. 3a and 3b may be continuously monitored in the detection unit 26, and the contamination status and the actual thickness of a contamination layer may be provided as a feed-back signal to the cleaning arrangement 27 via an electrical connection line 30. In such a way, the cleaning process may be stopped as soon as the contaminating substances are entirely removed from the EUV-reflective optical surface 6a, such that the jet 29 of cleaning gas does not react with the material of which the EUV-reflective optical surface 6a is made.

Figure 1B:
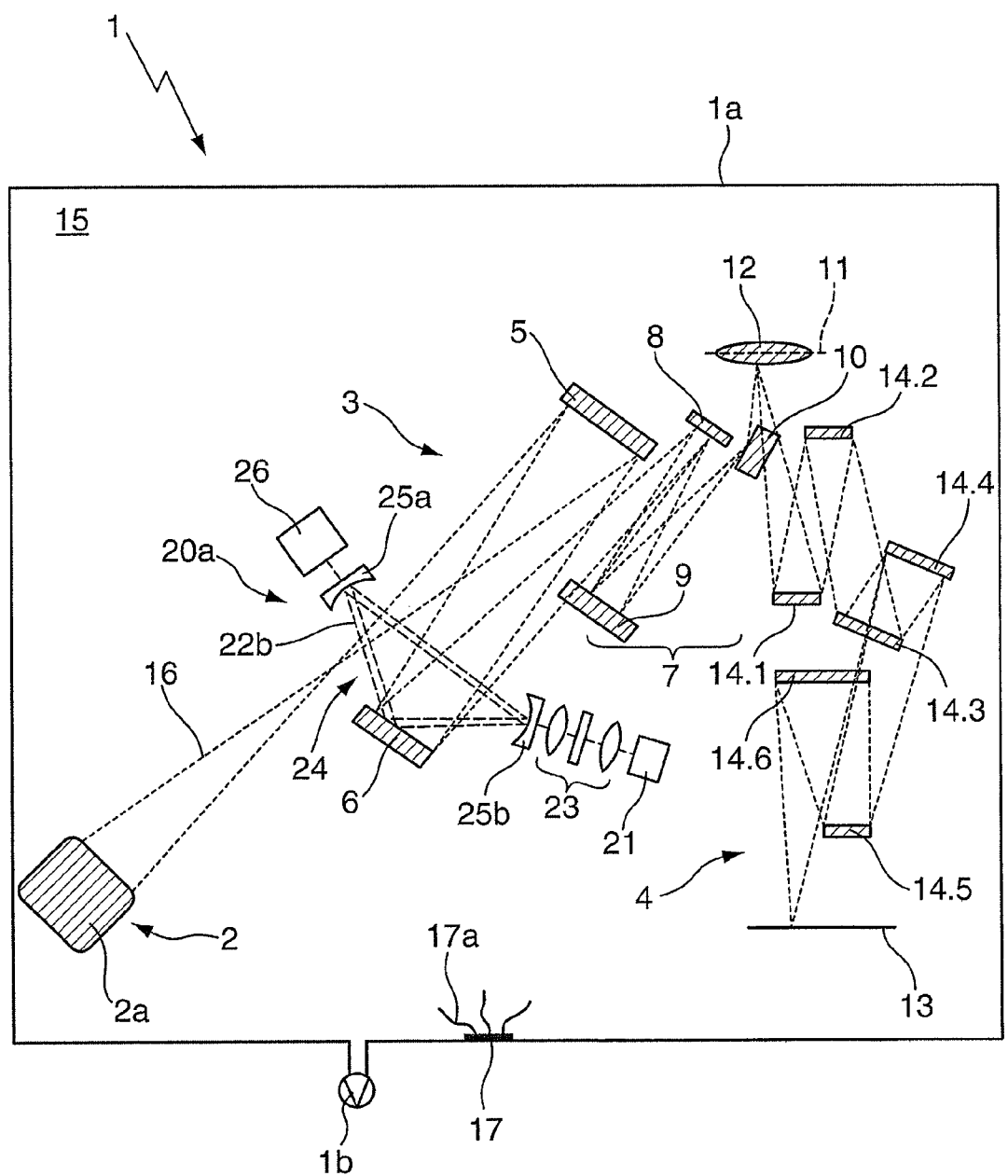

It will be understood that several variations for implementing the cavity ringdown reflectometer exist. For example, instead of using a linear optical resonator 24 in the cavity ringdown reflectometer 20 shown in FIG. 1a, a ring resonator 24a may be used in a cavity ringdown reflectometer 20a, as shown in FIG. 1b. The ring resonator 24a differs from the linear resonator 24 in that the optical path 22b between the EUV-reflective optical surface 6a and the mirrors 25a, 25b forms a closed loop. In such a way, the number of reflections inside the optical resonator 20a may be increased, thus also increasing the sensitivity of the measurement. The person skilled in the art will appreciate that instead of using three mirrors as shown in FIGS. 1a and 1b, four or more mirrors may be used to form the optical resonator 24, 24a.

Moreover, instead of determining the contamination status of the EUV-reflective optical surface 6a arranged in the optical path 16 of the EUV light source 2a by directly measuring its reflectivity, it is also possible to determine its contamination status by measuring the reflectivity of a further EUV-reflective surface 6b which is arranged adjacent to the EUV-reflective optical surface 6a, as will be explained with reference to FIG. 2 below, showing a further implementation of the cavity ringdown technique for the example of the mirror element 6.

In the mirror element 6, two multilayer systems 32, 32a are arranged on a common substrate 31. The respective multilayer systems 32, 32a, both comprise a plurality of alternating molybdenum and silicon layers, on the topmost layer (cap layer) of which the EUV-reflective surfaces 6a, 6b are formed. Contaminating substances in the form of carbon deposits 17a are deposited on both the EUV-reflective optical surface 6a and the further EUV-reflective optical surface 6b of the mirror element 6. The optical properties of the multilayer systems 32, 32a have been chosen to be identical, as typically both have been produced in the same coating process. The only difference between the EUV-reflective surface 6a and the further EUV-reflective surface 6b of the reflective optical element 6 is that the former is arranged in the optical path 16, while the latter is not. Consequently, the optical characteristics of the further EUV-reflective optical surface 6b do not influence the exposure process. Nevertheless, as the further EUV-reflective optical surface 6b is arranged adjacent to the optical path 16, the EUV radiation from the EUV light source 2a also impinges on the latter, such that the contamination status of the further EUV-reflective optical surface 6b is also indicative of the contamination status of the EUV-reflective optical surface 6a arranged within the optical path 16.

Figure 2:
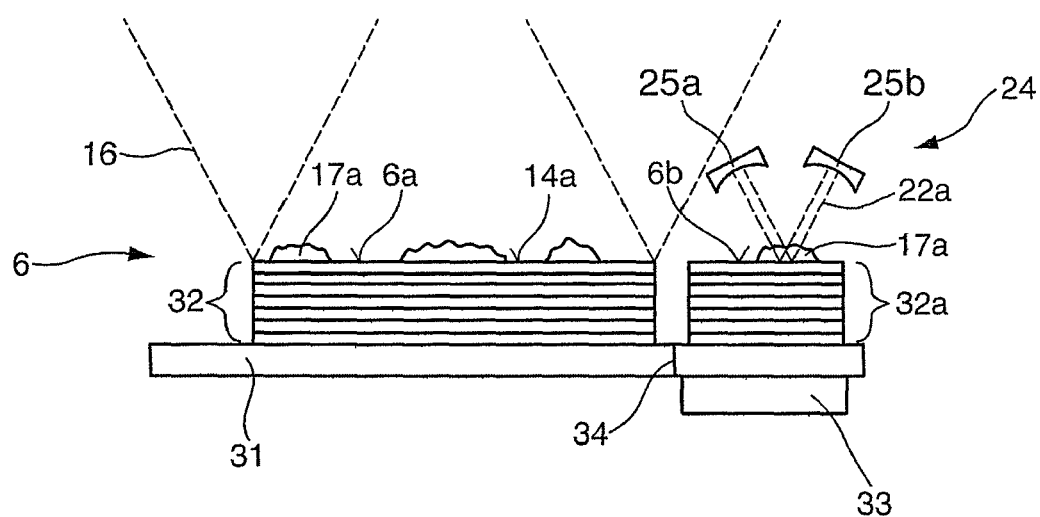
FIG. 2 is a diagrammatic view of an optical element having two EUV-reflective optical surfaces.

Therefore, by determining the contamination status of the further EUV-reflective optical surface 6b by using a cavity ringdown reflectometer of which only the optical resonator 24 is shown in FIG. 2, information about the contamination status of the EUV-reflective optical surface 6a may be obtained. In particular, it is possible to change the temperature T of the further EUV-reflective optical surface 6b by using a temperature adjusting unit 33 without influencing the exposure process. The temperature adjusting unit 33 may comprise a combined cooling/heating element using e.g. cooling fluids, heating elements and/or Peltier elements, and is disposed below the substrate 31 of the EUV-reflective optical element 6. For avoiding a temperature change on the part of the substrate 31 which is located beneath the multilayer system 32 of the EUV-reflective optical surface 6a, a thermally insulating layer 34 is arranged in the substrate 31.

By adjusting the temperature T of the further EUV-reflective optical surface 6b, similar to the adjustment of the measuring wavelength $\lambda_m$ of the laser radiation, it is possible to increase the sensitivity of the ring-down cavity measurement for individual contaminating substances, as different substances may be adsorbed on or desorbed from the optical surface depending on their condensation temperature T. In particular, a permanent screening for contaminating substances may be performed on the EUV-reflective optical surface 6b by continuously changing the measuring wavelength $\lambda_m$ and/or the temperature in a given range which is chosen in dependence of the contaminating substances for which the contamination status is to be determined. It will be understood that the further EUV-reflective optical surface 6b may alternatively be arranged on a separate element disposed close to the optical element 6, e.g. on a holder such as an aperture stop or a vacuum separation valve. In particular, it is also possible to perform the temperature adjustment on the optical surfaces of the other optical elements arranged in the optical paths 22a, 22b of the optical resonators 24, 24a, i.e., on the optical surfaces of the end mirrors 25a, 25b.

Figure 1C:
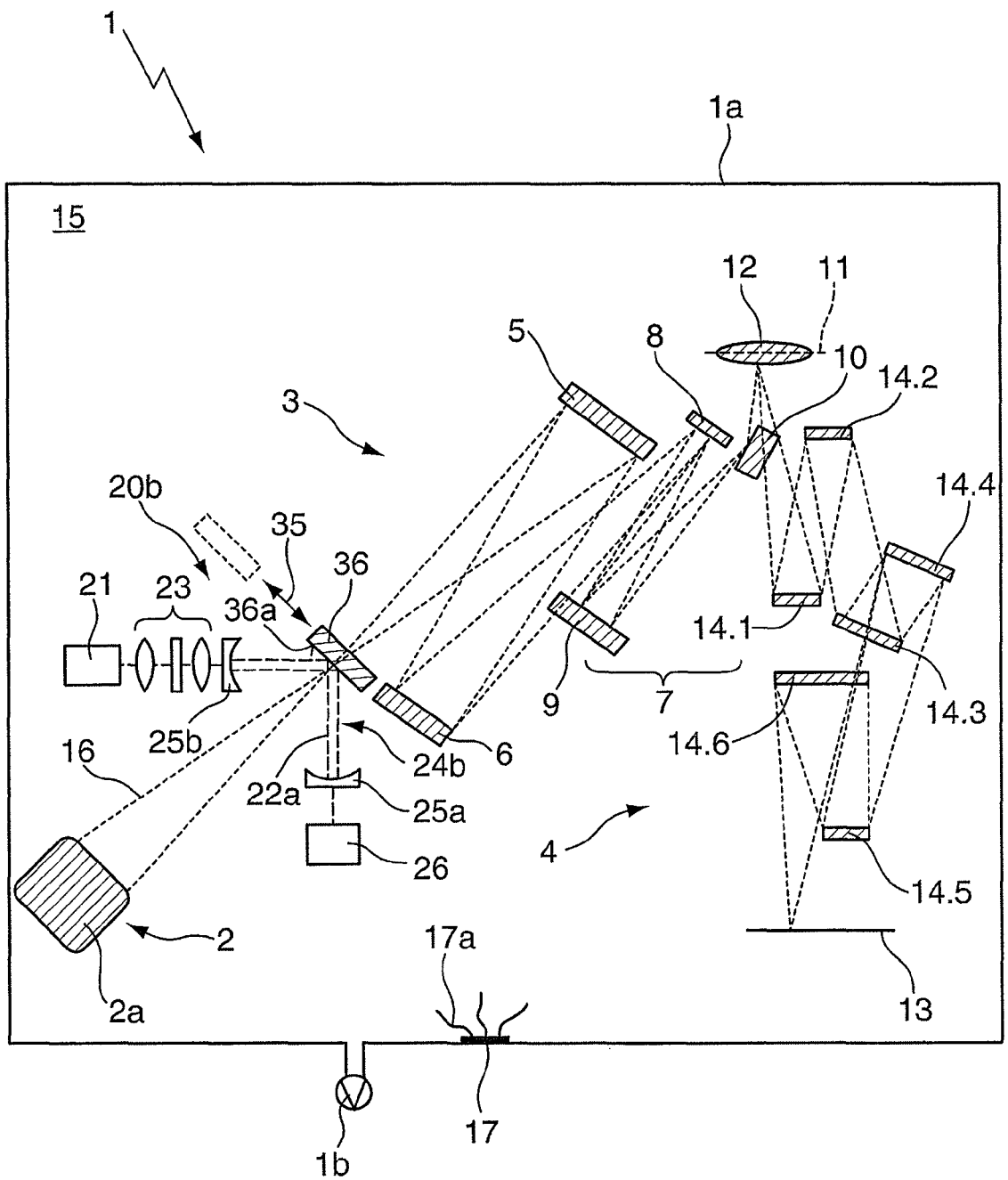

In a further embodiment of the EUV lithography apparatus shown 1 in FIG. 1c, the EUV reflective optical surface 36a is arranged on an optical element 36 which may be moved between a rest position located out of the optical paths 16, 22a of the EUV light source 2a and of an optical resonator 24b of a cavity ringdown reflectometer 20b and a measurement position in which the EUV-reflective surface 36a is arranged in both optical paths 16 and 22a. The transfer between both positions can be performed by a movement mechanism 35 which may be implemented, e.g., as an electrically driven swivel arm or any other suitable transport device known in the art.

During normal operation of the EUV lithography apparatus 1, i.e., during exposure of the wafer in the image plane 13, the optical element 36 is arranged in its rest position. Only during pauses of the exposure process may the optical element 36 be moved from the rest position to the measurement position which is located in an overlap region of the optical paths 16, 22a of the EUV light source 2a and of the optical resonator 24b. In such a way, when switching-on the EUV light source 2a, the contamination status of the EUV-reflective optical surface 36a may be determined under exposure to EUV radiation without the EUV-reflective optical surface 36a taking part in the exposure process. Consequently, the temperature of the EUV-reflective optical surface 36a may be changed in the way described above without the risk of degrading the optical performance of the EUV lithography apparatus 1.

In such a way, and in particular, when a vacuum in the EUV lithography apparatus 1 has to be (re-)established before the start-up of the exposure process, the EUV-reflective surface 36a may serve as a test surface for ensuring that the number of contaminants in the EUV lithography apparatus 1 is low enough to (re-)start the exposure process. If this is the case, the optical element 36 is moved back to its rest position and the exposure process may start over again.

In the measurement position, the EUV-reflective optical surface 36a is arranged in such a way that it blocks the optical path 16 from the EUV light source 2a to the optical elements 5, 6, 8, 9, 10, 12, 14.1 to 14.5 following the EUV-reflective optical element 36, thus protecting them from possible degradations caused by the exposure to EUV radiation when a large number of contaminants are present. It will be understood that the optical element 36 need not necessarily be located before the first reflective optical element 5 of the projection system 3, but may instead be arranged at an arbitrary location inside of the EUV lithography apparatus 1, preferably at an aperture stop or a vacuum separation valve in order to simplify the transfer to/from the measurement position.

In summary, by using cavity ringdown reflectometry, it is possible to determine the contamination status of EUV-reflective optical surfaces in an EUV lithography apparatus with high precision. The person skilled in the art will appreciate that it is not necessary to arrange the entire cavity ringdown reflectometer 20, 20a, 20b inside the housing 1a, as it may be sufficient to include only parts of the input optics 23 and components for decoupling the laser light from the optical resonator 24, 24a, 24b inside the housing 1a. Coupling/decoupling of the laser radiation from the laser light source 21 to the detection unit 26 is preferably performed by way of fibre optics.

The above description of the preferred embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

The invention claimed is:

1. An extreme-ultraviolet (EUV) lithography apparatus, comprising:
   at least one EUV-reflective optical surface and a cavity ringdown reflectometer adapted to determine the contamination status of the EUV-reflective optical surface for at least one contaminating substance by determining the reflectivity of the EUV-reflective optical surface for radiation at a measuring wavelength ($\lambda_m$), and
   a temperature adjusting unit for adjusting the temperature of at least one optical surface of an optical element of the optical resonator,
   wherein the temperature adjusting unit is adapted to adjust the temperature of at least one optical surface of an optical element of the optical resonator depending on the contaminating substance.

2. The EUV lithography apparatus according to claim 1, wherein the measuring wavelength ($\lambda_m$) is adjustable depending on the contaminating substance.

3. The EUV lithography apparatus according to claim 1, wherein the measuring wavelength ($\lambda_m$) is larger than 200 nm.

4. The EUV lithography apparatus according to claim 1, wherein the cavity ringdown reflectometer comprises an optical resonator and the EUV-reflective optical surface is arranged in the optical path of the optical resonator.

5. The EUV lithography apparatus according to claim 4, wherein the optical resonator is a ring resonator.

6. The EUV lithography apparatus according to claim 4, wherein the cavity ringdown reflectometer comprises a movement mechanism for moving the EUV-reflective optical surface into the optical path of the optical resonator.

7. The EUV lithography apparatus according to claim 1, wherein the cavity ringdown reflectometer comprises a laser source for generating the radiation at the measuring wavelength ($\lambda_m$) and a detection unit for measuring the intensity of the radiation reflected from the EUV-reflective surface.

8. The EUV lithography apparatus according to claim 1, wherein the EUV-reflective optical surface is exposed to EUV radiation.

9. The EUV lithography apparatus according to claim 1, wherein the EUV-reflective optical surface is arranged in an irradiated area outside of the optical path of an EUV light source.

10. The EUV lithography apparatus according to claim 1, further comprising a cleaning arrangement for cleaning at least one EUV-reflective optical surface, the cleaning arrangement being controlled depending on the contamination status of the EUV-reflective optical surface.

11. The EUV lithography apparatus according to claim 1, wherein the at least one optical surface of an optical element of the optical resonator is the EUV-reflective optical surface.

12. A method for determining the contamination status of at least one EUV-reflective optical surface arranged in an extreme-ultraviolet (EUV) lithography apparatus for at least one contaminating substance comprising determining the reflectivity of the EUV-reflective optical surface for radiation at a measuring wavelength ($\lambda_m$) using a cavity ringdown reflectometer,
   wherein the temperature (T) of at least one optical surface of an optical element of the optical resonator is adjusted depending on the contaminating substance.

13. The method according to claim 12, wherein the measuring wavelength ($\lambda_m$) is adjusted depending on the contaminating substance.

14. The method according to claim 12, further comprising moving the EUV-reflective optical surface into the optical path of an optical resonator of the cavity ringdown reflectometer.

15. The method according to claim 12, wherein the at least one optical surface of an optical element of the optical resonator is the EUV-reflective optical surface.

* * * * *

UNITED STATES PATENT AND TRADEMARK OFFICE
CERTIFICATE OF CORRECTION

| | | |
|---|---|---|
| PATENT NO. | : 8,054,446 B2 | Page 1 of 1 |
| APPLICATION NO. | : 12/196075 | |
| DATED | : November 8, 2011 | |
| INVENTOR(S) | : Dieter Kraus, Dirk Heinrich Ehm and Stefan-Wolfgang Schmidt | |

It is certified that error appears in the above-identified patent and that said Letters Patent is hereby corrected as shown below:

Column 6, line 51: delete "10,14.1" and insert -- 10, 14.1 -- therefor.

Column 7, line 2: delete "frequeancy" and insert -- frequency -- therefor.

Column 7, line 20: delete "wave-length" and insert -- wavelength -- therefor.

Column 10, line 6: delete "12,14.1" and insert -- 12, 14.1 -- therefor.

Signed and Sealed this

Twenty-seventh Day of November, 2012

David J. Kappos
*Director of the United States Patent and Trademark Office*